(12) United States Patent
Schoon et al.

(10) Patent No.: US 10,869,783 B2
(45) Date of Patent: Dec. 22, 2020

(54) METHOD FOR APPLYING ELASTIC STRANDS

(71) Applicant: Kimberly-Clark Worldwide, Inc., Neenah, WI (US)

(72) Inventors: Bradley W. Schoon, Oshkosh, WI (US); Chadwick I. Romzek, Neenah, WI (US); Erica F. Creighton, Sahuarita, AZ (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 159 days.

(21) Appl. No.: 16/084,827

(22) PCT Filed: Mar. 28, 2016

(86) PCT No.: PCT/US2016/024466
§ 371 (c)(1),
(2) Date: Sep. 13, 2018

(87) PCT Pub. No.: WO2017/171705
PCT Pub. Date: Oct. 5, 2017

(65) Prior Publication Data
US 2019/0076301 A1    Mar. 14, 2019

(51) Int. Cl.
*A61F 13/15* (2006.01)
*B29C 70/56* (2006.01)

(52) U.S. Cl.
CPC .. *A61F 13/15593* (2013.01); *A61F 13/15699* (2013.01); *B29C 70/56* (2013.01)

(58) Field of Classification Search
CPC ......... A61F 13/15593; A61F 13/15699; B29C 70/56
See application file for complete search history.

(56) References Cited

U.S. PATENT DOCUMENTS

| 5,643,396 | A | 7/1997 | Rajala et al. |
|---|---|---|---|
| 6,863,959 | B2 | 3/2005 | Welch et al. |
| 7,045,028 | B2 | 5/2006 | Betrabet et al. |
| 7,160,408 | B2 * | 1/2007 | Otsubo ............. A61F 13/15699 156/161 |
| 7,270,889 | B2 | 9/2007 | Campbell et al. |
| 8,163,824 | B2 | 4/2012 | Okazaki et al. |

(Continued)

FOREIGN PATENT DOCUMENTS

| EP | 1138297 B1 | 12/2008 |
|---|---|---|
| EP | 2309966 B1 | 7/2013 |

(Continued)

*Primary Examiner* — Vishal I Patel
(74) *Attorney, Agent, or Firm* — Kimberly-Clark Worldwide, Inc.

(57) ABSTRACT

A method of applying elastic members includes applying a construction adhesive; intermittently applying an elastic adhesive; positioning first and second elastics in an elongated condition such that a first portion of the elastics are positioned in contact with both the construction adhesive and the elastic adhesive in hold zones and a second portion of the elastics are positioned in contact with the construction adhesive but not the elastic adhesive in release zones; severing the elastics in the release zones; retracting the elastics through the construction adhesive in the release zones; and maintaining the elongation of the elastics in the hold zones.

12 Claims, 7 Drawing Sheets

(56) References Cited

U.S. PATENT DOCUMENTS

| | | |
|---|---|---|
| 8,921,474 B2 | 12/2014 | Alper et al. |
| 9,034,425 B2 | 5/2015 | Harris |
| 2004/0068246 A1 | 4/2004 | Rose et al. |
| 2012/0055615 A1* | 3/2012 | Back ................. A61F 13/15601 156/177 |
| 2014/0350155 A1 | 11/2014 | Hamann et al. |
| 2014/0364532 A1 | 12/2014 | Dubois et al. |
| 2015/0024649 A1 | 1/2015 | Czaplewski et al. |
| 2015/0032072 A1 | 1/2015 | Hashimoto et al. |
| 2015/0223990 A1 | 8/2015 | Armstrong-Ostle et al. |
| 2016/0113825 A1 | 4/2016 | Bianchi et al. |
| 2016/0121014 A1 | 5/2016 | Remmers et al. |

FOREIGN PATENT DOCUMENTS

| | | |
|---|---|---|
| EP | 2659867 A1 | 11/2013 |
| WO | WO2006130218 A1 | 12/2006 |
| WO | WO12053945 A1 | 4/2012 |

* cited by examiner

METHOD FOR APPLYING ELASTIC STRANDS

BACKGROUND OF THE INVENTION

Bonded structures are incorporated into a variety of articles, including personal care products, medical garments, and industrial work wear garments, for example. Adhesives have traditionally been used to bond individual layers of an absorbent article, such as top sheets, back sheets, intake layers, flaps, ears, and the like. Adhesives have also traditionally been used to bond discrete pieces of an absorbent article, such as fasteners, leg elastics, waist elastics, and the like. In personal care products, such as absorbent underwear, bond strength and bond integrity are important around the absorbent core. In personal care products, bond strength is also important to maintain elastics in a tensioned condition as the elasticized areas of disposable garments can be exposed to considerable tension while the garments are being worn. If a bond failure or a bond gap between the top sheet and the back sheet occurs in the area around the absorbent core, there is a possibility that absorbent material positioned between the top sheet and the back sheet may escape from the garment. If a bond failure occurs with a tensioned elastic component, the gasketing performance of the product may suffer. As such, there is a need for a high speed intermittent process for securely applying elastic members in select areas while providing good bond integrity, strength, and coverage around the absorbent core with minimal application of adhesives.

SUMMARY OF THE INVENTION

In a first aspect, the present invention is directed to a method of applying elastic members. The method includes providing a back sheet web having a first lateral side edge and a second lateral side edge. The back sheet web defines a back sheet width extending from the first lateral side edge to the second lateral side edge.

The method further includes providing a top sheet web having a first lateral side edge and a second lateral side edge. The top sheet web defines a top sheet width extending from the first lateral side edge to the second lateral side edge.

The method further includes providing a plurality of discrete absorbent cores and providing a first elastic member web and a second elastic member web.

The method further includes applying a first adhesive in a first adhesive pattern to define a first adhesive width. The first adhesive width is at least 90% the top sheet width or the back sheet width.

The method further includes intermittently applying a second adhesive in a second adhesive pattern to define alternating hold zones and release zones. The second adhesive has a different composition and properties than the first adhesive.

The method further includes positioning the first elastic member web, the second elastic member web, the first adhesive, the second adhesive, and the discrete absorbent cores between the top sheet web and the back sheet web to define an absorbent insert web. The first elastic member web and the second elastic member web are in an elongated condition and a first portion of the first elastic member web and a first portion of the second elastic member web are positioned in contact with the first adhesive and the second adhesive in the hold zones. A second portion of the first elastic member web and a second portion of the second elastic member web are positioned in contact with the first adhesive but not the second adhesive in the release zones.

The method further includes severing the first elastic member web and the second elastic member web in the release zones to define first and second discrete elastic members.

The method further includes retracting the second portions of the first elastic member and the second elastic member through the first adhesive in the release zones and maintaining the elongation of the first portions of the first elastic member and the second elastic member in the hold zones.

In various embodiments, the method can further include applying the first elongated elastic member web and the second elongated elastic member web in elastic patterns having curved portions separated by straight portions. In various embodiments, the discrete absorbent cores define a width having a narrowed portion and the curved portions of the elastic patterns align with the narrowed portion of the absorbent cores.

In various embodiments, the method can further include aligning the curved portions of the elastic patterns with the hold zones and aligning the straight portions of the elastic patterns with the release zones.

In various embodiments, the elastic member web defines a width in the cross-machine direction and the second adhesive application defines a second adhesive application width defined in the cross machine direction and the adhesive application width is at least twice the elastic member web width.

In various embodiments, the first adhesive is a construction adhesive made of poly alpha olefin and the second adhesive is an elastic adhesive made of a styrenic block copolymer.

In various embodiments, the second adhesive overlays the first adhesive in the hold zones once assembled in the absorbent insert web. In various embodiments, the method can further include applying the first adhesive in a slot coat application at an add-on of 1 to 3 gsm and applying the second adhesive in a swirl pattern at an add-on of 8 to 12 gsm. In various embodiments, the method can further include applying the first adhesive in a slot coat pattern having a plurality of voids extending in a machine direction. Each void can have a width of 0.75 to 1.25 mm.

In various embodiments, the first elongated elastic member web and the second elongated elastic member web are each applied in an elastic pattern having a portion that is at least partially overlaid by the absorbent cores once assembled in the absorbent insert web. In various embodiments, the method can further include severing and retracting the first elongated elastic member web and the second elongated elastic member web such that the portion that is at least partially overlaid by the absorbent core is untensioned.

In various embodiments, the method can further include supplying a first body panel web and a second body panel web, separating the absorbent insert web at lines of weakness located between the discrete absorbent cores to define discrete absorbent inserts, attaching the discrete absorbent inserts to the first body panel web and the second body panel web to define a composite garment web, folding the composite garment web, attaching the first body panel web to the second body panel web along a series of garment side seam bonds, and cutting the composite garment web at the garment side seam bonds to create a plurality of pant-like disposable absorbent garments.

In another aspect, the present invention provides a method of applying intermittent elastic members. The method includes providing a liquid impermeable back sheet web having a first lateral side edge and a second lateral side edge. The back sheet web defines a back sheet width extending from the first lateral side edge to the second lateral side edge.

The method further includes providing a liquid permeable top sheet web having a first lateral side edge and a second lateral side edge. The top sheet defines a top sheet width extending from the first lateral side edge to the second lateral side edge.

The method further includes providing a plurality of discrete absorbent cores having a first lateral side edge and a second lateral side edge. The discrete absorbent cores define a width extending from the first lateral side edge to the second lateral side edge. The width has a narrowed portion.

The method further includes providing a first elongated elastic member web and a second elongated elastic member web and applying a first adhesive to the top sheet web in a first adhesive application. The first adhesive application is a slot coat application defining a first adhesive application width in a cross-machine direction. The first adhesive application width is at least 90% the top sheet width.

The method further includes intermittently applying a second adhesive in a second adhesive pattern to define alternating hold zones and release zones. The second adhesive has a different composition and properties than the first adhesive.

The method further includes applying a third adhesive to the back sheet web in a third adhesive pattern defining a third adhesive application width in the cross-machine direction. The third adhesive application width is less than 70% of the back sheet width and is applied in a central portion of the back sheet web.

The method further includes positioning the first elastic member web, the second elastic member web, the first adhesive, the second adhesive, the third adhesive, and the discrete absorbent cores between the top sheet and the back sheet to define an absorbent insert web. The first elastic member web and the second elastic member web are each positioned in an elongated condition and have a first pattern and a second pattern respectively. The first and second patterns each have a curved portion and a straight portion. The curved portions of the first pattern and the second pattern are aligned with the narrowed portion of the discrete absorbent cores. The discrete absorbent cores are positioned in a central portion of the absorbent insert web and are spaced apart in the direction of travel to define endseals between adjacent absorbent cores. The first elastic member web is positioned in a first lateral portion of the absorbent insert web and is in contact with both the first adhesive and the second adhesive in the hold zones. The first elastic member web is in contact with the first adhesive, but not the second adhesive, in the release zones. The second elastic member web is positioned in a second lateral portion of the absorbent insert web and is in contact with both the first adhesive and the second adhesive in the hold zones. The second elastic member web is in contact with the first adhesive, but not the second adhesive, in the release zones.

The method further includes weakening the absorbent insert web at lines of weakness between discrete absorbent cores to define discrete absorbent inserts.

The method further includes severing the first elastic member web and the second elastic member web in the release zones to define first and second discrete elastic members.

The method further includes retracting the first elastic member and the second elastic member in the release zones through the first adhesive and maintaining the elongation of the first elastic member and the elongation of the second elastic member in the hold zones.

In various embodiments, the first adhesive and the third adhesive are poly alpha olefin adhesives and the second adhesive is a styrenic block copolymer adhesive.

In various embodiments, the second adhesive overlays the first adhesive in the hold zones once assembled in the absorbent insert web.

In various embodiments, the first adhesive application and the third adhesive application are continuous applications.

In another aspect, the present invention provides a method of applying intermittent elastic members. The method includes providing a liquid impermeable back sheet web having a first lateral side edge and a second lateral side edge. The back sheet web defines a back sheet width extending from the first lateral side edge to the second lateral side edge.

The method further includes providing a liquid permeable top sheet web having a first lateral side edge and a second lateral side edge. The top sheet web defines a top sheet width extending from the first lateral side edge to the second lateral side edge.

The method further includes providing a plurality of discrete absorbent cores having a first lateral side edge and a second lateral side edge. The discrete absorbent cores define a width extending from the first lateral side edge to the second lateral side edge. The width has a narrowed portion.

The method further includes providing a first elongated elastic member web and a second elongated elastic member web.

The method further includes applying a first adhesive to the top sheet web in a continuous first adhesive application. The first adhesive is a construction adhesive and the first adhesive application is a slot coat application defining a first adhesive application width in a cross-machine direction. The first adhesive application width is at least 90% the top sheet width.

The method further includes intermittently applying a second adhesive to the back sheet web in a second adhesive pattern to define alternating hold zones and release zones. Each hold zone and each release zone have a length. The second adhesive is an elastic adhesive and has a different composition and properties than the first adhesive.

The method further includes applying a third adhesive to the back sheet web in a third adhesive pattern. The third adhesive is a construction adhesive and the third adhesive pattern is a swirl application defining a third adhesive application width in the cross-machine direction. The third adhesive application width is less than 70% of the back sheet width and is applied in a central portion of the back sheet web.

The method further includes positioning the first elastic member web, the second elastic member web, the first adhesive, the second adhesive, the third adhesive, and the discrete absorbent cores between the top sheet and the back sheet to define an absorbent insert web. The first elastic member web and the second elastic member web are each positioned in an elongated condition and have a first pattern and a second pattern respectively. The first and second patterns each have curved portions and straight portions. The curved portions of the first pattern and the second pattern are aligned with the narrowed portion of the discrete absorbent cores. The discrete absorbent cores are positioned in a central portion of the absorbent insert web and are spaced apart in the direction of travel to define endseals between adjacent absorbent cores. The first elastic member web is positioned in a first lateral portion of the absorbent insert web and is in contact with both the first adhesive and the second adhesive in the hold zones. The first elastic member web is in contact with the first adhesive, but not the second adhesive, in the release zones. The second elastic member web is positioned in a second lateral portion of the absorbent insert web and is in contact with both the first adhesive and the second adhesive in the hold zones. The second elastic member web is in contact with the first adhesive, but not the second adhesive, in the release zones.

The method further includes perforating the absorbent insert web at lines of weakness between the discrete absorbent cores to define discrete absorbent inserts having a discrete absorbent insert length.

The method further includes severing the first elastic member web and the second elastic member web in the release zones to define first and second discrete elastic members. The hold zone length is less than the absorbent insert length.

The method further includes retracting the first elastic member and the second elastic member in the release zones by dragging a portion of the first elastic member and a portion of the second elastic member through the first adhesive and maintaining the elongation of the first elastic member and the elongation of the second elastic member in the hold zones.

The method further includes transporting the perforated absorbent insert web to a separation device.

The method further includes separating the absorbent insert web at the perforations to define discrete absorbent inserts.

The method further includes supplying a first body panel web and a second body panel web, attaching the discrete absorbent inserts to the first body panel web and the second body panel web to define a composite garment web, folding the composite garment web, attaching the first body panel web to the second body panel web along a series of garment side seam bonds, and cutting the composite garment web at the garment side seam bonds to create a plurality of pant-like disposable absorbent garments.

In various embodiments, the first adhesive is an APAO adhesive and the second adhesive comprises a styrenic block copolymer. In various embodiments, the first adhesive is a construction adhesive comprising poly alpha olefin and having an add-on of 1 to 3 gsm and the second adhesive is an elastic adhesive comprising a styrenic block copolymer and having an add-on of 8 to 12 gsm.

BRIEF DESCRIPTION OF THE DRAWINGS

FIG. 6A is a cross-sectional view of FIG. 6 taken along the line 6a-6a.

DETAILED DESCRIPTION OF THE DRAWINGS

Figure 1:
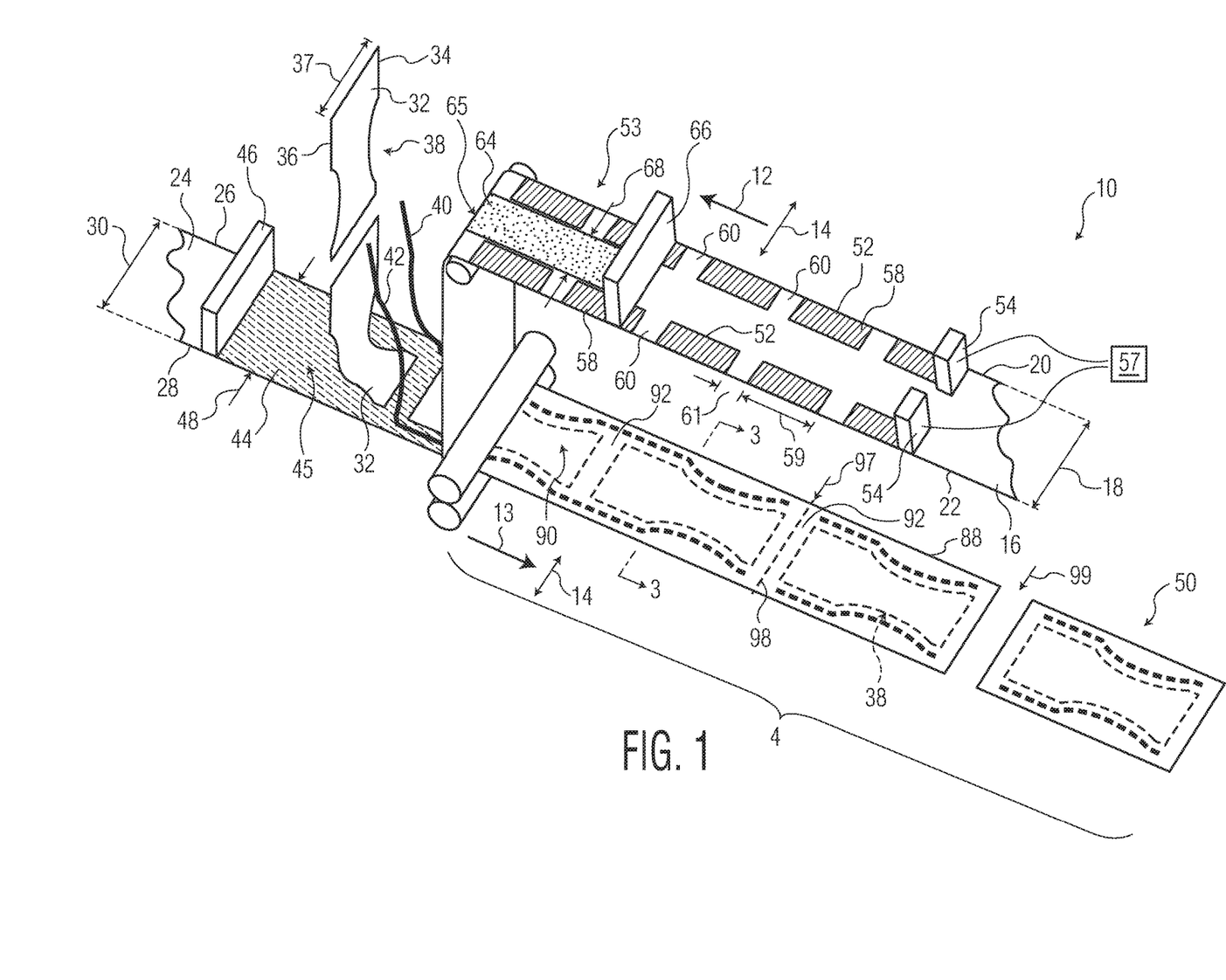
FIG. 1 is a perspective view of an exemplary method of the present invention illustrating absorbent cores having a first exemplary core shape and elastic member webs having a first exemplary elastic pattern.
Figure 2:
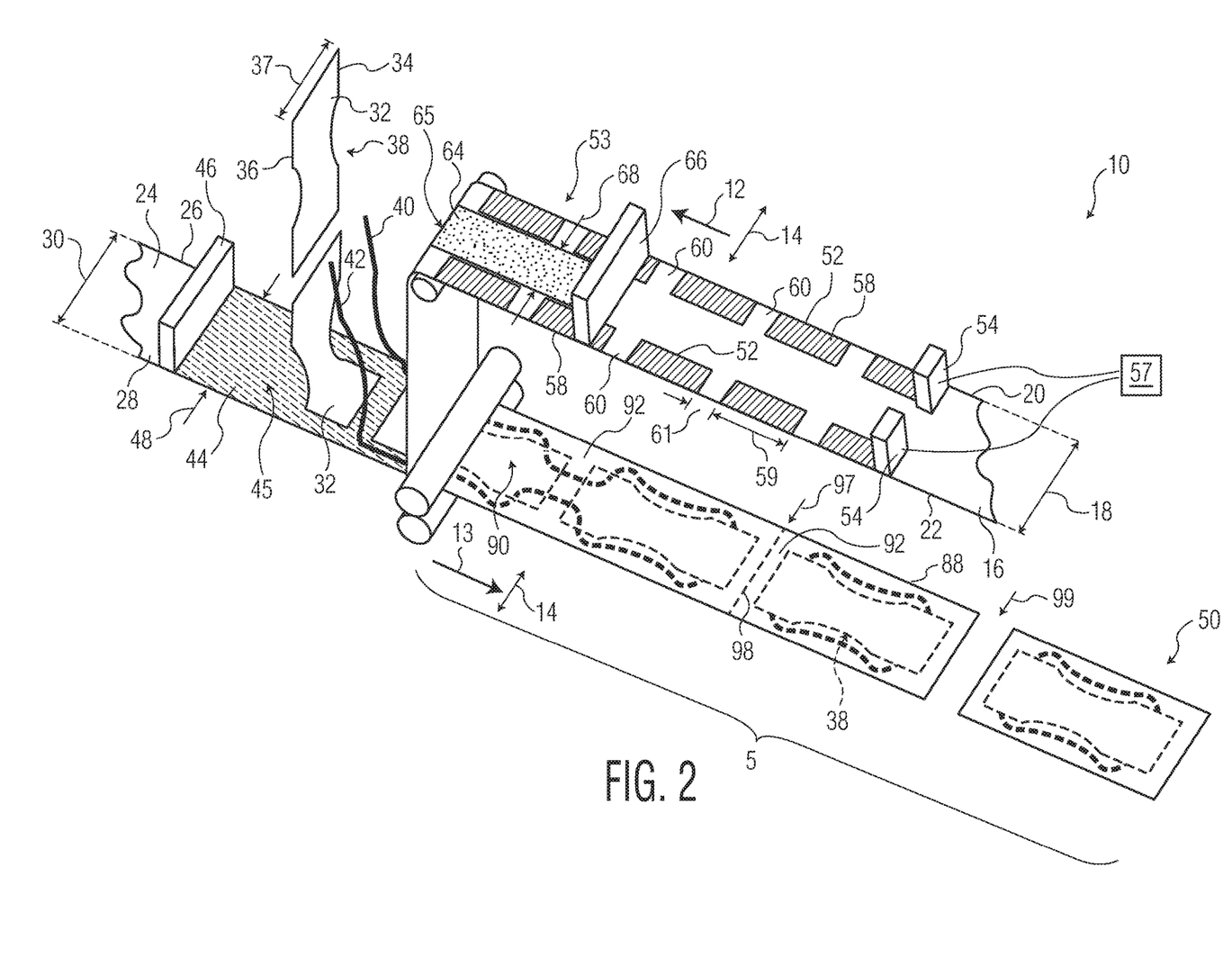
FIG. 2 is a perspective view of another exemplary method of the present invention illustrating absorbent cores having a second exemplary core shape and elastic member webs having a second exemplary elastic pattern.
Figure 3:
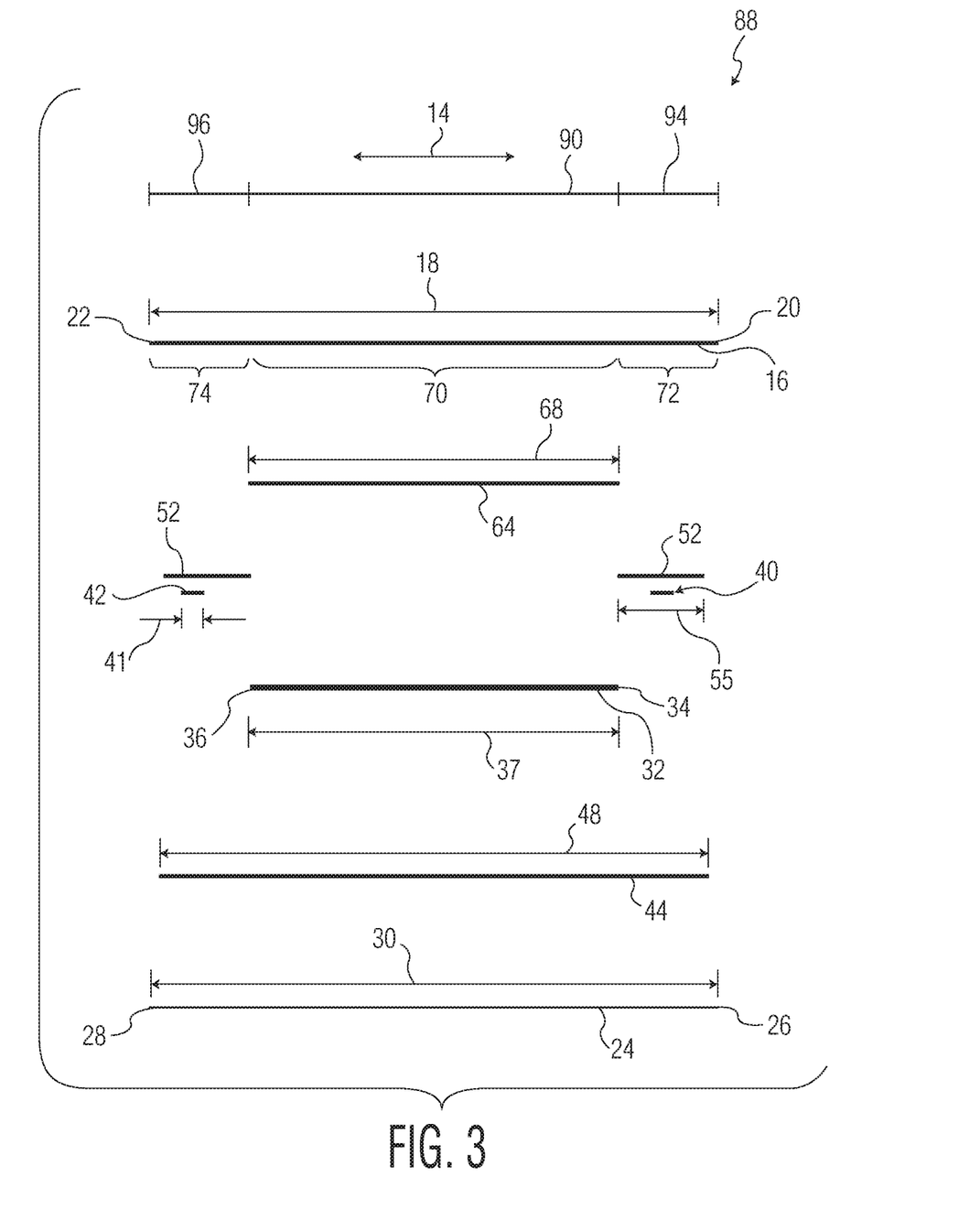
FIG. 3 is an expanded cross-sectional view of the method of FIG. 1 taken along the line 3-3.

The present invention includes a method of applying elastic members to moving webs to create absorbent inserts. An exemplary absorbent insert assembly method 10 is illustrated in FIGS. 1-3. FIG. 1 is a perspective view of the method 10 illustrating absorbent cores having a first exemplary core shape and elastic member webs having a first exemplary elastic pattern. FIG. 2 is a perspective view of the method 10 illustrating absorbent cores having a second exemplary core shape and elastic member webs having a second exemplary elastic pattern. FIG. 3 is a cross-sectional view of FIG. 1 taken along the line 3-3. The method 10 includes providing a back sheet web 16 moving in a direction of travel 12 and having a first lateral side edge 20 and a second lateral side edge 22. The back sheet web 16 defines a back sheet web width 18 which extends from the first lateral side edge 20 to the second lateral side edge 22. The back sheet web width 18 is measured in a cross-machine direction 14, which is perpendicular to the direction of travel 12. The back sheet web 16 also defines a central portion 70, a first lateral zone 72 between the central portion 70 and the first lateral side edge 20, and a second lateral zone 74 between the central portion 70 and the second lateral side edge 22 as illustrated in FIG. 3.

The method 10 further includes providing a top sheet web 24 moving in a direction of travel 13 and having a first lateral side edge 26 and a second lateral side edge 28. The top sheet web 24 defines a top sheet web width 30 extending from the first lateral side edge 26 to the second lateral side edge 28. The top sheet web width 30 is measured the cross-machine direction 14 which is perpendicular to the direction of travel 13. The relative orientation of the top sheet web 24 and the back sheet web 16 during processing is not necessarily indicative of the relative orientation during use. In use, the top sheet web is typically oriented to face the wearer and provide a body side surface. The back sheet web is typically oriented to face away from the wearer and provide a garment side surface. In some embodiments (not illustrated), the top sheet web can be positioned on top of the back sheet web during various stages of manufacturing.

The back sheet web 16 can include a material that is substantially liquid-impermeable, and can be elastic, stretchable or non-stretchable. The back sheet web 16 can be a single layer of liquid-impermeable material, but can also include a multi-layered laminate in which at least one of the layers is liquid-impermeable. One or more layers of the back sheet web 16 can be both liquid and vapor-impermeable, or can be liquid-impermeable and vapor-permeable. A liquid-impermeable layer can be manufactured from a thin plastic film, although other flexible liquid-impermeable materials can also be used.

The top sheet web 24 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, reticulated thermoplastic films, apertured formed thermoplastic films, apertured plastic films, hydroformed thermoplastic films, thermoplastic scrims, or the like. Various woven and nonwoven fabrics can be used for the top sheet web 24. For example, the top sheet web 24 can be composed of a meltblown or spunbonded web of polyolefin fibers. The top sheet web 24 can also be a bonded-carded web composed of natural and/or synthetic fibers. The top sheet web 24 can be liquid permeable. The top sheet web 24 can be composed of a substantially hydrophobic material, and the hydrophobic material can, optionally, be treated with a surfactant or otherwise processed to impart a desired level of wettability and hydrophilicity. Optionally, the top sheet web 24 can be treated with lotion or ointment.

The method 10 also includes providing a plurality of discrete absorbent cores 32. The absorbent cores 32 have a first lateral side edge 34 and second lateral side edge 36. The absorbent cores 32 define a width 37 extending from the first lateral side edge 34 to the second lateral side edge 36. In some embodiments, the absorbent core width 37 can have a narrowed portion 38. The narrowed portion 38 can be adapted and positioned to align with the wearer's crotch and legs during use for improved comfort and fit. Depending on the product design, the narrowed portion 38 can be generally centered in the absorbent cores 32 as illustrated in FIG. 2 or can be skewed towards one end as illustrated in FIG. 1. For example, a product designed primarily for women can have the narrowed portion 38 of the absorbent core 32 generally centered to better align the absorbent core 32 with the female anatomy during use wherein the absorbent material is generally centered in the final product. Likewise, a product designed primarily for men can have the narrowed portion 38 of the absorbent core 32 generally skewed towards one end to better align the absorbent core 32 with the male anatomy during use wherein more of the absorbent material can be shifted forward in the final product.

The absorbent cores 32 can be any structure which is generally compressible, conformable, non-irritating to the wearer's skin, and capable of absorbing and retaining liquids and certain body wastes. The absorbent core 32 can be manufactured in a wide variety of sizes and shapes, and from a wide variety of liquid absorbent materials commonly used in the art. For example, the absorbent core 32 can suitably include a matrix of hydrophilic fibers alone, such as a web of cellulosic fluff, or a mixture of both hydrophilic and hydrophobic fibers, or the fibers can be mixed with particles of a high-absorbency material commonly known as superabsorbent material. The absorbent core 32 can also include other absorbent components that are often used in absorbent articles, such as a dusting layer, a wicking or acquisition layer, a surge layer and/or a secondary top sheet. In a particular embodiment, the absorbent assembly includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly to better contain and absorb body exudates. The concentration of the superabsorbent particles can also vary through the thickness of the absorbent assembly. Alternatively, the absorbent assembly can include a laminate of fibrous webs and superabsorbent material or other suitable means of maintaining a superabsorbent material in a localized area. Typically, a superabsorbent material is capable of absorbing at least about 10 times its weight in physiological saline, and desirably is capable of absorbing more than about 25 times its weight in physiological saline.

The method 10 also includes providing a first elastic member web 40 and a second elastic member web 42. The first elastic member web 40 and/or the second elastic member web 42 can be any suitable elastomeric material for providing retractive forces and/or gathers in absorbent articles. For example, the elastic member webs 40, 42 can be elastic ribbons, strands, threads, and the like suitable for use in disposable absorbent garments are known in the art, one example being LYCRA brand elastic filaments, available from Invista having offices in Wichita, Kans. In some embodiments, the elastic member webs 40, 42 each include 1, 2, 3, 4, 5, or more strands of elastic. In various embodiments, the elastic member webs 40, 42 can be elastic strands having a decitex of 400 to 700. In various embodiments, the elastic member webs 40, 42 can be elongated at least 100%, at least 200%, or at least 300% of their non-tensioned length. In some embodiments, the elastic member webs 40, 42 can each include 3 strands of elastic having a decitex of at least 600, e.g., 620 decitex, and an elongation of 250%. In some embodiments, the elastic member webs 40, 42 can each include 5 strands of elastic having a decitex of at least 450, e.g., 470 decitex, and an elongation of 200%. In some embodiments, the elastic member webs 40, 42 can each include 5 strands of elastic having a decitex of at least 500, e.g., 540 decitex, and an elongation of 200%.

The method 10 further includes positioning the first elastic member web 40, the second elastic member web 42, and the discrete absorbent cores 32 between the top sheet web 24 and the back sheet web 16 to define an absorbent insert web 88. The absorbent insert web 88 defines a first lateral portion 94, a central portion 90, and second lateral portion 96 as illustrated in FIG. 3.

The method 10 also includes applying a first adhesive 44 in a first adhesive pattern 45 to define a first adhesive width 48 using a first adhesive application 46. The first adhesive width 48 can have any suitable absolute width and can have any suitable relative width as compared to the top sheet web width 30 or as compared to the back sheet web width 18. The first adhesive application 46 can be a continuous application or can be an intermittent application relative to the direction of travel 13. In some embodiments, the first adhesive width 48 can be at least 70%, at least 80%, or at least 90% of the top sheet web width 30 or the back sheet web width 18. In some embodiments the first adhesive width 48 can be 100% the top sheet web width 30 or 100% the back sheet web width 18. For example, in embodiments adapted for use by females, the first adhesive width 48 can be 175 to 225 mm, 185 to 215 mm, 195 to 205 mm, or 200 mm and the top sheet web width 30 can be 200 to 240 mm, 210 to 230 mm, 215 to 225 mm, or 220 mm and the back sheet web width 18 can be 195 to 225 mm, 200 to 215 mm, or 206 mm.

For example, in embodiments adapted for use by males, the first adhesive width 48 can be 225 to 275 mm, 235 to 265 mm, 245 to 255 mm, or 250 mm and the top sheet web width 30 can be 245 to 285 mm, 255 to 275 mm, 260 to 270 mm, or 268 mm and the back sheet web width 18 can be 245 to 275 mm, 250 to 265 mm, or 254 mm.

The first adhesive 44 can be applied to the top sheet web 24 as illustrated in FIGS. 1 and 2 or can be applied to the back sheet web 16 (not illustrated) using any suitable application technique including melt-spraying, slot-coating, or swirl-spraying. In some embodiments, the method 10 includes applying the first adhesive 44 to the top sheet web 24 in a first adhesive application 46, wherein the first adhesive application 46 is a slot coat application defining a first adhesive application width 48 in the cross-machine direction 14, wherein the first adhesive application width 48 is at least 90% the top sheet width 30 as illustrated in FIG. 3.

In some embodiments, the first adhesive application 46 is a slot coat application defining a first adhesive pattern 45 having ribbons of adhesive separated by voids extending in the direction of travel 13. In some embodiments, the voids extend in the direction of travel 13 and each void has a width of 0.75 to 1.25 mm. In some embodiments, each ribbon of adhesive has a width of 0.75 to 1.25 mm. In some embodiments, the first adhesive application 46 applies the first adhesive 44 at an add-on of 1 to 3, 1.25 to 2.5, or 1.35 to 1.55 grams per square meter (gsm). In some embodiments adapted for use by females, the first adhesive application 46 applies the first adhesive 44 at an add-on of 1.4 to 1.6 or 1.5 gsm. In some embodiments adapted for use by males, the first adhesive application 46 applies the first adhesive 44 at an add-on of 1.3 to 1.4 or 1.35 gsm.

The method 10 also includes intermittently applying a second adhesive 52 in a second adhesive pattern 53 using a second adhesive application 54. The second adhesive pattern 53 can include intermittent adhesive applications which in turn define hold zones 58 and release zones 60 wherein the hold zones 58 alternate with the release zones 60. Each hold zone 58 has a length 59 and each release zone 60 has a length 61 as measured in the direction of travel 12. The second adhesive application 54 can be applied to the back sheet web 16 as illustrated in FIGS. 1 and 2 or can be applied to the top sheet web 24 (not illustrated). When applied to the back sheet web 16, the second adhesive application 54 can be applied in both the first lateral zone of the back sheet web 72 and the second lateral zone of the back sheet web 74. In some embodiments, the second adhesive application 54 can be applied directly to the first elastic member web 40 and/or the second elastic member web 42 using any suitable method, such as strand coating.

In various embodiments, the second adhesive application 54 can include a single applicator having multiple adhesive delivery modules. In other embodiments, the second adhesive application 54 can include two or more applicators as illustrated in FIGS. 1 and 2. The intermittent second adhesive application 54 can include one or more controllers 57 for selectively actuating (e.g., turning on and off) the second adhesive application 54. Turning the second adhesive application 54 on and off creates the hold zones 58 (*on*) and the release zones 60 (off).

In some embodiments, the second adhesive application 54 includes applying the second adhesive 52 in a swirl pattern at an add-on of 6 to 16, 8 to 12, 9 to 10 or 9 gsm. In some embodiments, the second adhesive pattern 53 defines hold zones 58 having a length 59 of 200 to 350 mm, 225 to 325 mm, 240 to 250, or 295 to 310. In some embodiments adapted for females, the hold zones 58 have a length of 240 to 250 or 246 mm. In some embodiments adapted for males, the hold zones 58 can have a length of 275 to 325 or 300 mm. In various embodiments, the hold zones 58 can have a width 55 of 30 to 50, 35 to 45, or 40 to 43 mm. Likewise, the first elastic member web 40 and the second elastic member web 42 each define an elastic member width 41 as measured in the cross-machine direction 14 as illustrated in FIG. 3. In various embodiments, the hold zone width 55 may be equal to or greater than the elastic member width 41. In some embodiments, the hold zone width 55 may be at least twice the elastic member width 41. This relative width difference allows for a linear application of the second adhesive 52 in the direction of travel while still providing adequate coverage for a curved application of the first and the second elastic members 40, 42.

In some embodiments, the second adhesive pattern 53 defines release zones 60 having a length 61 of 140 to 210 mm. In some embodiments adapted for females, the release zones 60 can have a length 61 of 190 to 210 or 200 mm. In some embodiments adapted for males, the release zones 60 can have a length 61 of 130 to 150 or 144 mm. In some embodiments adapted for use by males, the hold zones 58 can have a length 59 of 300 mm and the release zones 60 can have a length 61 of 144 mm. In some embodiments adapted for use by females, the hold zones 58 can have a length 59 of 246 mm and the release zones 60 can have a length 61 of 200 mm.

The method 10 can optionally include applying a third adhesive 64 in a third adhesive pattern 65 using a third adhesive application 66. The third adhesive application 66 can be applied to the back sheet web 16 as illustrated in FIGS. 1 and 2. In other embodiments, not illustrated, the first adhesive application 46 can be applied to the back sheet web 16 and the third adhesive application 66 can be applied to the top sheet web 24. The third adhesive application 66 can be a spray, swirl, slot coat, or any other suitable application. The third adhesive application 66 can be a continuous application or can be an intermittent application relative to the direction of travel 12. The third adhesive application 66 defines a third adhesive application width 68 as measured in the cross-machine direction 14. The third adhesive application width 68 can be defined relative to the back sheet web width 18. In some embodiments, the third adhesive application width 68 is approximately equal to the back sheet web width 18. In other embodiments, the third adhesive application width 68 is less than 90%, less than 80%, less than 70%, less than 60%, or less than 50% the back sheet web width 18. In various embodiments, the third adhesive application 66 can be applied to the central portion 70 of the back sheet web 16 as illustrated.

In some embodiments, the third adhesive application 66 includes applying the third adhesive 64 in a swirl pattern at an add-on of 1 to 4, 2 to 3, or 2.8 gsm. In some embodiments, the third adhesive pattern 65 has a width 68 of 90 to 130, 100 to 120, or 115 mm.

The first adhesive 44 and/or the third adhesive 64 are construction adhesives for assembling the components of the absorbent insert web 88 together. The first adhesive 44 and/or the third adhesive 64 can be made of any suitable construction adhesive as is known in the art of absorbent article manufacturing. In general, the first adhesive 44 and/or the third adhesive 64 have a lower crystallinity and a higher loss modulus at higher frequency as compared to the second adhesive 52. For example, the first adhesive 44 and/or the third adhesive 64 can be a poly alpha olefin (PAO), such as amorphous poly alpha olefin (APAO) or tackified amorphous poly alpha olefin (tAPAO). These adhesives can be produced using Ziegler-Natta catalysis and can include a variety of monomers such as propylene, ethylene and butene. In general, these adhesives have a very low degree of crystallinity as measured by Differential Scanning calorimetry (DSC).

The first adhesive 44 and/or the third adhesive 64 can include an adhesive composition having an APAO in an amount between about 50 percent and about 99 percent, or between about 70 percent and about 95 percent, or between about 80 percent and about 85 percent by weight of the adhesive composition. Examples of suitable APAO polymers include propylene copolymerized with butene, ethylene, and/or hexene. Two suitable neat APAO are polypropylene-1-butene APAO random copolymers, such as RT2730 or RT2723, both available from REXtac having offices in Odessa, Tex. The first adhesive 44 and/or the third adhesive 64 can also include a tackifier in an amount between about 1 percent and about 50 percent, or between about 5 percent and about 30 percent, or between about 15 percent and about 20 percent by weight of the adhesive composition. In contrast with the APAO, the tackifier has a low molecular weight, suitably about 2000 Daltons or less. Examples of suitable tackifiers include fully or substantially saturated (e.g. hydrogenated) C5 resins, derived from isoprene or di-cyclopentadiene (DCPD). Other suitable tackifiers include hydrocarbons derived from petroleum distillates, rosin, rosin esters, hydrogenated rosin esters, polyterpenes derived from wood, polyterpenes derived from synthetic chemicals, as well as combinations of any of these. Additionally, the adhesive composition can include an antioxidant stabilizer, suitably in an amount sufficient for maintaining the desired properties of adhesives. Sufficient amounts of antioxidant stabilizer would be apparent to one skilled in the art. For example, the adhesive composition can include an antioxidant stabilizer in an amount of about 1 percent or less by weight of the adhesive composition.

In various embodiments, the first adhesive 44 and/or the third adhesive 64 can be construction adhesive with a tackified APAO adhesive composition consisting wholly or essentially of APAO and tackifier, with a minor amount of antioxidant. Alternatively, one or more additives can be present in the construction adhesive in an amount of about 20 percent or less by weight of the adhesive composition. These additives can include a plasticizer, color pigment or dye, fragrance, filler, a polymer compatibilizer, and/or a low softening point additive. The adhesive composition can include any one or more of these additives. Examples of suitable color pigments and fillers include $TiO_2$, carbon black, and calcium carbonate. Examples of suitable polymer compatibilizers include polypropylene-b-polyethylene, polypropylene-b-polybutene diblock copolymers. Additionally, one or more viscosity modifiers can be added to the adhesive composition. Examples of suitable viscosity modifiers include waxes, oils, low molecular weight polymers, and other viscosity modifiers known to those skilled in the art. In some embodiments, the first adhesive 44 and/or third adhesive 64 can be the adhesive designated RT-8723 available from REXtac having offices in Odessa, Tex.

In general, the second adhesive 52 is an elastic attachment adhesive for joining and holding the first elastic member web 40 and the second elastic member web 42 in an elongated condition in the absorbent insert web 88. The second adhesive 52 can be any suitable adhesive as is known in the art of absorbent article manufacturing that has good cohesive strength and high creep resistance. The second adhesive 52 generally has a higher crystallinity, higher glass transition temperature, and/or higher concentration of styrene as compared to the first adhesive 44 and/or the third adhesive 64. The second adhesive 52 is generally stiffer (not as tacky), higher in cohesive strength, and/or has a shorter open time as compared to the first adhesive 44 and/or the third adhesive 64.

In various embodiments, the second adhesive 52 can be a hot melt adhesive based on polymers such as polyolefins (ethylene- or propene-based polymers), or polyolefins (ethylene or propene copolymers) with oxygen containing monomers, or styrenic block copolymers containing at least one rubbery phase, like styrene-isoprene-styrene (SIS), or styrene-butadiene-styrene (SBS) polymers. Styrenic block copolymers have dual characteristics including the cohesion of the styrenic phase associated with the rubber behavior of another phase. In some embodiments, the second adhesive 52 can include a SIS/SBS blend.

In some embodiments, the second adhesive 52 can be characterized by capillary-viscosity or hardness as those characteristics are described in U.S. Pat. No. 7,045,028 granted May 16, 2006, to Betrabet et al. In some embodiments, the second adhesive 52 can have a capillary-viscosity value of about 7 Pas·sec or greater and/or a Shore-OO-Hardness value of about 65 or greater. In other embodiments, the second adhesive 52 can have a capillary-viscosity value of about 9 Pas·sec or greater and/or a Shore-OO-Hardness value of about 90 or greater.

In some embodiments, the second adhesive 52 can be characterized by its styrene content. For example, in some embodiments, the second adhesive 52 can have a styrene content greater than 35% by weight or can have a styrene content of 38% to 50% by weight. In some embodiments, the second adhesive 52 can have 35-50% by weight of styrene in a linear SBS block copolymer. In some embodiments, the second adhesive 52 can be the adhesive designated H20171 or H2717 available from Bostik having offices in Wauwatosa, Wis.

Figure 4:
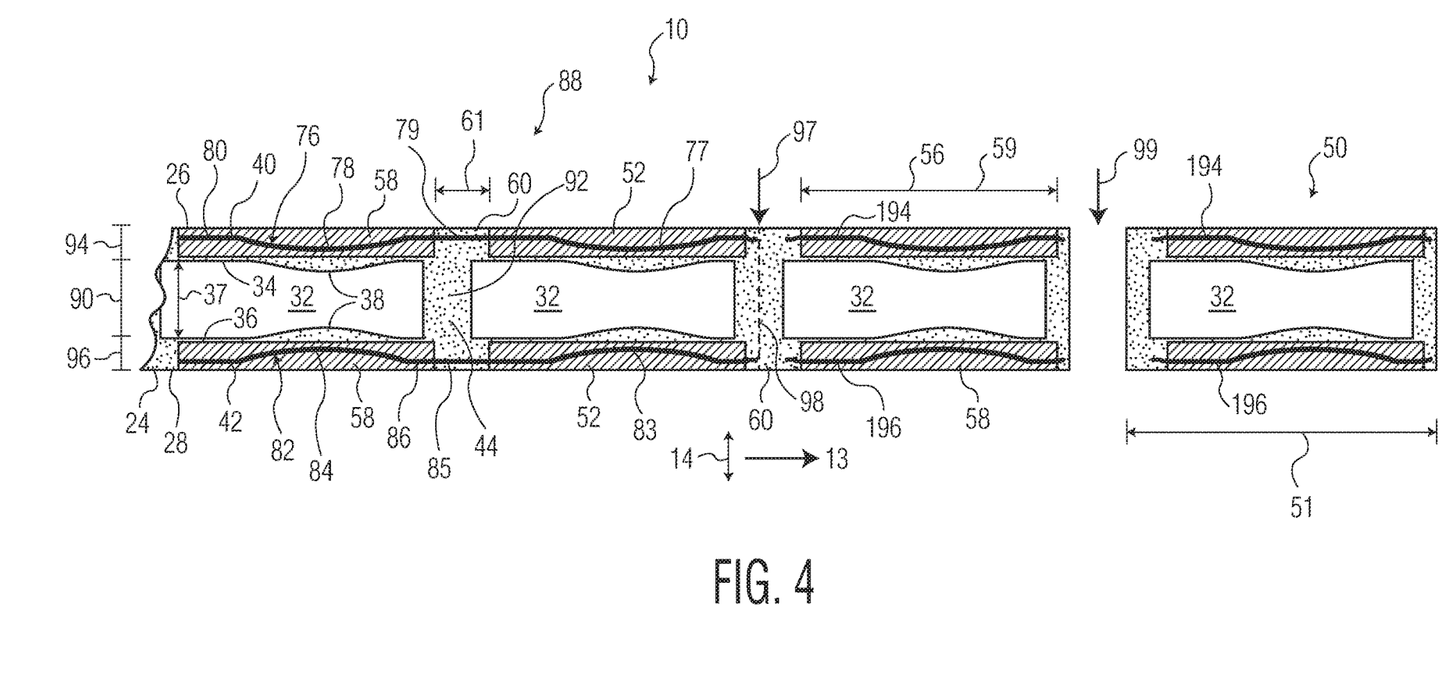
FIG. 4 is a top view of a portion of the method of FIG. 1 with some elements omitted for clarity.
Figure 5:
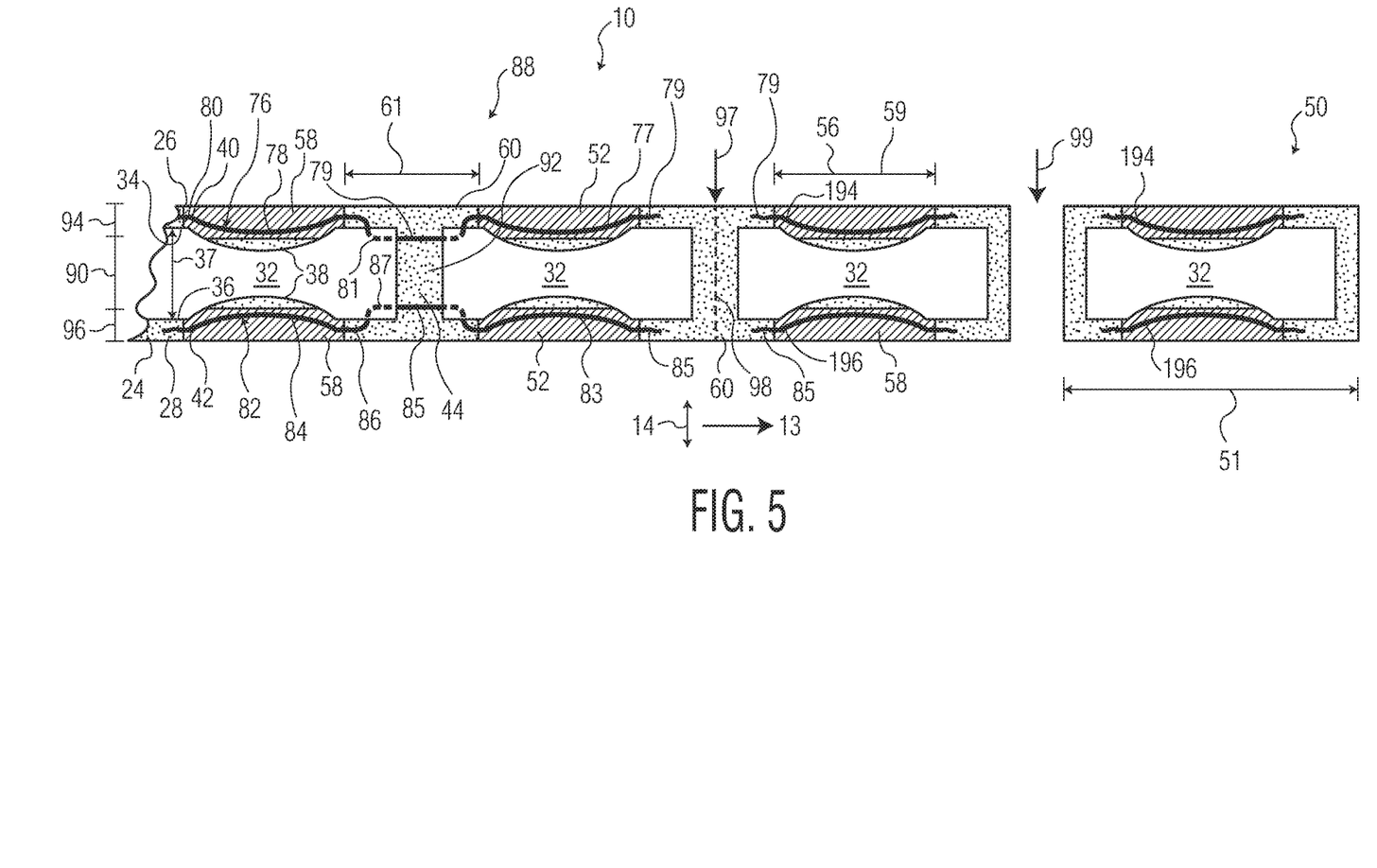
FIG. 5 is a top view of a portion of the method of FIG. 2 with some elements omitted for clarity.

The discrete absorbent cores 32, the first elastic member web 40, the second elastic member web 42, the first adhesive 44, and the second adhesive 52 can be positioned in any suitable location and configuration within the absorbent insert web 88 as illustrated in FIGS. 4 and 5. FIG. 4 is a top plan view of the portion 4 of the method 10 of FIG. 1 with the back sheet web 16 and the optional third adhesive 64 omitted to better illustrate underlying features. Likewise, FIG. 5 is a top plan view of the portion 5 of the method 10 of FIG. 2 with the back sheet web 16 and the optional third adhesive 64 omitted.

In some embodiments, the discrete absorbent cores 32 are positioned in a central portion 90 of the absorbent insert web 88 and are spaced apart in the direction of travel 13 to define end seals 92 between adjacent absorbent cores 32. In some embodiments, the first elastic member web 40 and/or the second elastic member web 42 can be extended in the direction of travel 13. In some embodiments, the first elastic member web 40 is positioned in the first lateral portion 94 of the absorbent insert web 88 and the second elastic member web 42 is positioned in the second lateral portion 96 of the absorbent insert web 88.

In some embodiments, the first elongated elastic member web 40 can be applied in a first elastic pattern 76 having curved portions 78 separated by straight portions 80. Likewise, the second elongated elastic member web 42 can be applied in a second elastic member pattern 82 having curved portions 84 separated by straight portions 86.

In some embodiments, the discrete absorbent cores define a width 37 having a narrowed portion 38 and the curved portion 78 of the first elastic pattern 76 and the curved portion 84 of the second elastic pattern 82 aligns with the narrowed portion 38 of the absorbent cores 32 as illustrated in FIGS. 4 and 5. In some embodiments, the method 10 can further include aligning the curved portions 78, 84 of the elastic patterns 76, 82 with the hold zones 58 and aligning the straight portions 80, 86, at least partially, with the release zones 60 as illustrated in FIGS. 4 and 5.

In some embodiments, the first elongated elastic member web and/or the second elongated elastic member web can be applied in elastic patterns having portions that are at least partially overlaid by the absorbent cores once assembled in the absorbent insert web 88. For example, FIG. 5 representatively illustrates the first elongated elastic member web 40 having a portion 81 being overlaid by the absorbent cores 32. Likewise, FIG. 5 illustrates the second elongated elastic member web 42 having a portion 87 being overlaid by the absorbent cores 32.

A first portion 77 of the first elastic member web 40 and a first portion 83 of the second elastic member web 42 are positioned in contact with both the first adhesive 44 and the second adhesive 52 in the hold zones 58. A second portion 79 of the first elastic member web 40 and a second portion 85 of the second elastic member web 42 are positioned in contact with the first adhesive 44 and can be positioned to avoid contact with the second adhesive 52 in the release zones 60 as illustrated in FIGS. 4 and 5.

The method 10 also includes the step of severing the first elastic member web 40 and/or the second elastic member web 42 in the release zones 60 to define first discrete elastic members 194 and second discrete elastic members 196. In the illustrated embodiments, the second adhesive application length 56 is less than the absorbent insert length 51 so the method 10 also includes the step of retracting the second portions 79, 85 of the first elastic member 194 and the second elastic member 196 through the first adhesive 44 in the release zones 60 and maintaining the elongation of the first portions 77, 83 of the first elastic member 40 and the second elastic member in the hold zones 58. In these embodiments, the hold zone length 59 plus the release zone length 61 equals the absorbent insert length 51. In embodiments adapted for use for females, the hold zone length 59 can be 40 to 70, 50 to 60, or 54 to 56% the absorbent insert length 51. In embodiments adapted for use for males, the hold zone length 59 can be 50 to 75, 55 to 75, 60 to 73, or 66 to 68% the absorbent insert length 51.

In some embodiments, wherein the first elastic member web 40 and/or the second elastic member web 42 are at least partially overlaid by the absorbent cores 32, the step of severing the first elastic member web 40 and/or the second elastic member web 42 to define a first discrete elastic members 194 and a second discrete elastic members 196 includes the step of retracting the second portions 79, 85 through the first adhesive 44 and at least partially from under the absorbent cores 32 as illustrated in FIG. 5. In these embodiments, the second portions 79, 85, which include the overlaid portions 81, 87, are untensioned after severing.

The severing and retracting step is enabled by use of construction adhesive as the first adhesive 44 in a sufficient add-on to allow the first discrete elastic member 194 and the second discrete elastic member 196 to pull or drag through the first construction adhesive 44 during retraction. However, the first construction adhesive 44 in the end seals 92 is sufficient to bond the top sheet and the back sheet to prevent absorbent material from escaping the absorbent insert web 88 or the absorbent insert 50. Likewise, the maintaining step is enabled by use of elastic adhesive as the second adhesive 52 in sufficient add-on to prevent the first discrete elastic member 194 and the second discrete elastic member 196 from pulling, snapping, or creeping through the hold zones 58. However, excessive add-on of the first adhesive 44 can prevent the first discrete elastic member 194 and/or the second discrete elastic member 196 from pulling or dragging through the construction adhesive in the end seals 92 and can result in inconsistent intermittent elastics with some continuous elastic strands.

The method 10 can further include weakening the absorbent insert web at lines of weakness 98 formed between the discrete absorbent cores 32 to define discrete absorbent inserts 50 having a discrete absorbent insert length 51. The lines of weakness 98 are formed in the top sheet web 24 and/or the back sheet web 16 and can be produced by thinning, compressing, perforating, cutting, scoring, or the like, or combinations thereof to define the discrete absorbent inserts 50. The step of weakening the absorbent assembly web 88 and the step of severing the elastic member webs can be two separate operations or can be completed in the same operation and/or using the same mechanism. In one embodiment, a weakening station 97 can include a knife roll and an anvil roll positioned to form a cutting nip. The knife roll can be adapted to both perforate the absorbent insert web 88 and sever the first elastic member web 40 and the second elastic member web 42 in the release zones 60 to allow the elastics to retract in the end seal 92 but maintain the absorbent web 88 for further processing.

The method 10 can further include separating the absorbent insert web 88 between the discrete absorbent cores 32 at a separation station 99 to release the discrete absorbent inserts 50 for packaging or further assembly. The step of separating the absorbent insert web 88 into discrete absorbent inserts 50 can be an integral step with the weakening step or can be a separate operation. For example, in some embodiments, the weakening step and the separating step are two distinct operations wherein the perforated absorbent insert web is transported to the separation station 99 at some point further along the process. In some embodiments, the separation station 99 breaks the absorbent insert web 88 at the lines of weakness 98 to separate the discrete absorbent inserts 50.

The absorbent insert webs and the absorbent inserts of the present invention can be used as final products or can be further processed for inclusion in any suitable absorbent article. For example, in some embodiments, the absorbent insert webs and/or the absorbent inserts of the present invention can be used as a component in a training pant adapted for use by children or in absorbent underwear adapted for use by adults.

Figure 6:
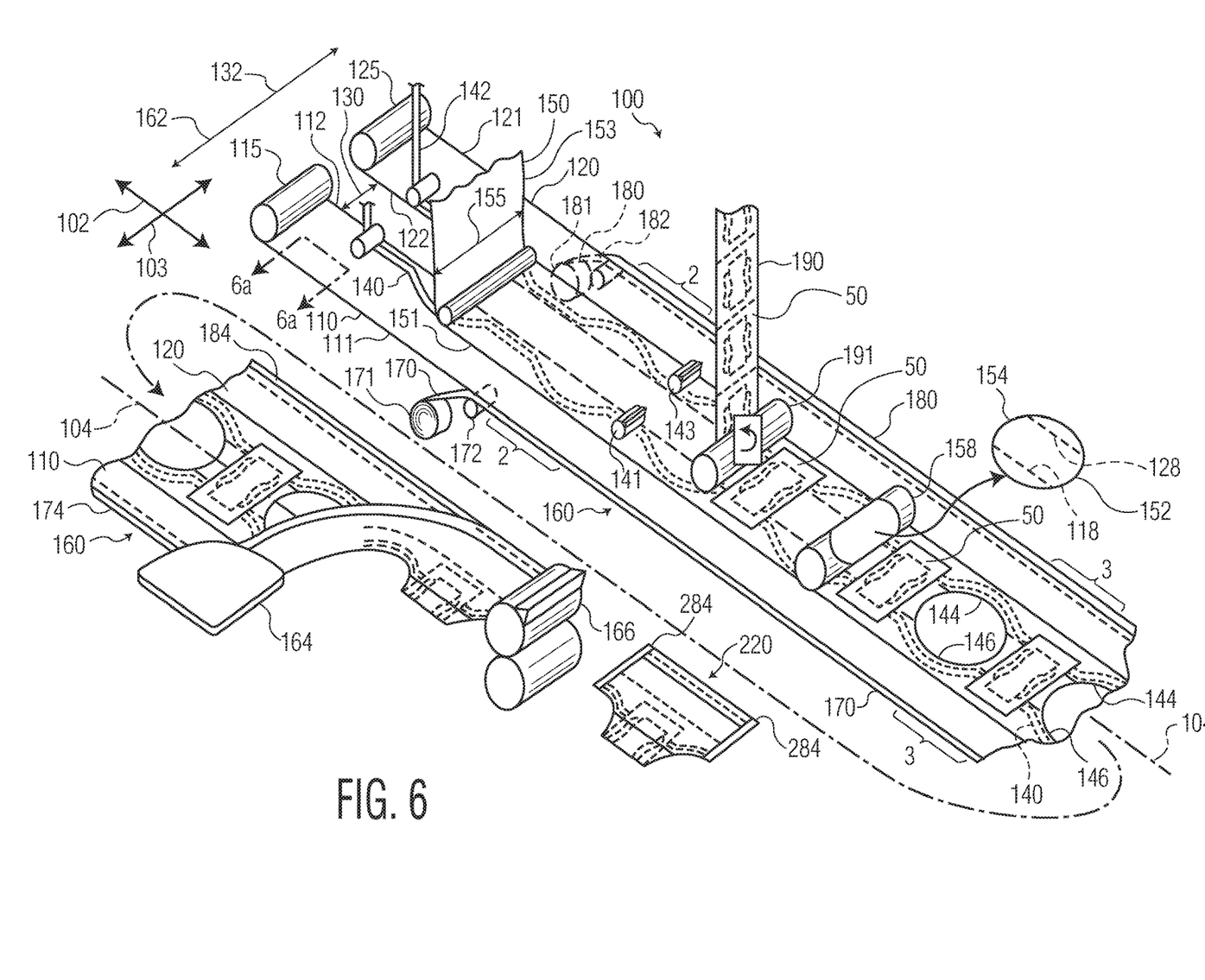
FIG. 6 is a perspective view of an exemplary garment assembly process of the present invention.
Figure 6A:
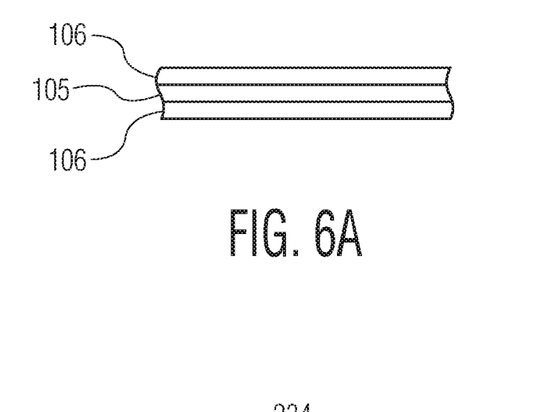

For purposes of illustration, the absorbent insert webs of the present invention will be illustrated in an exemplary garment assembly method for making absorbent underwear suitable for use by adults. As representatively illustrated in FIG. 6, a garment assembly method 100 can include supplying an elastomeric laminate first body panel web 110 (such as via roll supply 115) and an elastomeric laminate second body panel web 120 (such as via roll supply 125), both webs traveling in a machine direction 102. The first body panel web 110 can be spaced from the second body panel web 120 in a cross-machine direction 103. The first body panel web 110 and/or the second body panel web 120 can have any suitable configuration. For example the first body panel web 110 and/or the second body panel web 120 can be laminate webs having one or more nonwoven facing layers and an elastomeric layer. The elastomeric layer can be made of stranded elastics, elastic films, and the like, and combinations thereof. In the illustrated embodiment, the elastomeric laminate first body panel web 110 and the elastomeric film laminate second body panel web 120 each comprise an elastomeric layer 105 and at least one nonwoven layer. As illustrated in FIG. 6A, the elastomeric film layer 105 can be sandwiched between two nonwoven layers 106, 106. FIG. 6A is a cross-sectional view of the method 100 of FIG. 6 taken along the line 6a-6a. U.S. Patent Application Publications US 2008/0095978 and US 2009/0197041, both assigned to Kimberly-Clark Worldwide, Inc. and incorporated by reference herein to the extent not inconsistent herewith, provide examples of technology suitable for use in creating elastomeric film laminates suitable for use with the present invention, although other elastomeric laminates can also be used.

In particular embodiments, the elastomeric laminate first body panel web 110 defines a waist edge 111 that extends in the machine direction 102 and a leg edge 112 that extends in the machine direction 102. Similarly, the elastomeric laminate second body panel web 120 in particular embodiments defines a waist edge 121 that extends in the machine direction 102 and a leg edge 122 that extends in the machine direction 102. The method further can comprise positioning the first and second body panel webs 110/120 in a non-overlapping relationship such that their respective leg edges 112/122 are spaced apart from each other in a cross-machine direction 103 a first distance 130 and their respective waist edges 111/121 are spaced apart from each other in the cross-machine direction 103 a second distance 132.

In particular embodiments, the method can further include supplying a continuous first leg elastic member 140 and/or a continuous second leg elastic member 142, both leg elastic members 140/142 traveling in the machine direction 102. Each leg elastic member 140/142 can comprise a single ribbon, strand, or thread (or the like) of elastic material, or each can comprise two (as shown in the example of FIG. 6), three, or more ribbons, strands, or threads (or the like) of elastic material. The garment assembly method 100 can further include attaching the first leg elastic member 140 to the first body panel web 110 and attaching the second leg elastic member 142 to the second body panel web 120. In some embodiments, as representatively illustrated in FIG. 6, the first leg elastic member 140 is attached to the first body panel web 110 at least partially adjacent the leg edge 112 of the first body panel web 110, and the second continuous leg elastic member 142 is attached to the second body panel web 120 at least partially adjacent the leg edge 122 of the second body panel 120. In some embodiments, the first leg elastic member 140 can extend in the machine direction 102 in a straight-line path (not shown), and the second leg elastic member 142 can extend in a non-straight-line path in the machine direction 102. In other embodiments, such as that representatively illustrated in FIG. 6, both the first leg elastic member 140 and the second leg elastic member 142 can extend in a non-straight-line path in the machine direction 102. Elastic ribbons, strands, threads, and the like suitable for use in disposable absorbent garments are known in the art, one example being LYCRA brand elastic filaments, available from Invista having offices in Wichita, Kans. In certain embodiments, it can be desirable to reduce or eliminate the ability of the elastic strands to impart gathering forces in selected regions of an absorbent garment. For example, if it is desired to reduce or eliminate the gathering capacity of the elastic strands in the laterally central region of the garment (such as over the absorbent insert 50), the elastic strands can be severed or otherwise deadened to decrease or eliminate the retractive forces in select areas. In some embodiments, the elastic strands can be severed one or more times using first leg elastic chopper 141 and second leg elastic chopper 143, so that the elastic strands "snap back" a selected distance and such that the elastic strands do not pass over the laterally central region of the garment with tension as illustrated in FIG. 6.

The garment assembly method 100 can further include supplying a continuous leg elastic covering web 150 traveling in the machine direction 102. The leg elastic covering web 150 can comprise, for example, any suitable nonwoven material, such as spunbond, spunbond-meltblown laminates, bonded-carded webs, and the like. In particular embodiments, such as that representatively illustrated in FIG. 6, the leg elastic covering web 150 defines a first edge 151, a second edge 153, and a width 155 extending between the first edge 151 and the second edge 153 in the cross-machine direction, and the covering web width 155 is greater than the first distance 130 and less than the second distance 132. After superposing the leg elastic covering web 150 over (or under) the first and second body panel webs 110/120, the garment assembly method 100 can further include attaching the leg elastic covering web 150 to both the first body panel web 110 and the second body panel web 120 so as to sandwich the first leg elastic member 140 between the first body panel web 110 and the leg elastic covering web 150 and so as to sandwich the second leg elastic member 142 between the second body panel web 120 and the leg elastic covering web 150, thereby creating a composite web 160. The composite web defines a composite web width 162 which extends in the cross-machine direction 103, which is the width between the two transversely outermost edges of the composite process web assembly. In particular embodiments, the composite web width 162 is greater than the cross-machine direction width 155 of the leg elastic covering web 150.

In particular embodiments, the garment assembly method 100 can comprise supplying a first waistband web 170 (such as via roll supply 171) and a second waistband web 180 (such as via roll supply 181), and can further comprise attaching the first waistband web 170 to the first body panel 110 (such as at attachment station 172) and attaching the second waistband web 180 to the second body panel 120 (such as at attachment station 182). The waistband webs can be inherently elastomeric (such as via the use of an elastomeric film laminate material). Alternatively, waist elastic strands could be affixed to the front and/or back waistband webs to impart elasticity thereto. For example, the waistband webs could be inherently non-elastomeric but made to be elastomeric by affixing elastic strands thereto (such as by sandwiching elastic strands between two nonwoven webs or by enveloping elastic strands within a single, "C-folded" nonwoven web).

The garment assembly method 100 can in particular embodiments further comprise removing portions 152 of the leg elastic covering web 150. In addition, the garment assembly method 100 can further include removing portions 128 of the second body panel web 120, removing portions 118 of the first body panel web 110, or removing both portions 128 of the second body panel web 120 and portions 118 of the first body panel web 110. Removal of portions 128 of the second body panel web 120 defines a series of back leg opening edges 144 spaced apart in the machine direction 102. Similarly, removal of portions 118 of the first body panel web 110 defines a series of front leg opening edges 146 spaced apart in the machine direction 102. It can be seen that in the example representatively illustrated in FIG. 6, the removed portion 154 of the composite web 160 includes a removed portion 152 of the covering web 150, a removed portion 118 of the first body panel web 110, and a removed portion 128 of the second body panel web 120. In addition or in the alternative to removal of portions 118/128 of the front and/or back body panel webs, particular embodiments of the method can include removing portions of the absorbent inserts 50 (not shown). Removal of the various portions can be accomplished by known techniques, such as via cutter unit 158.

The garment assembly method 100 can further include providing a supply 190 of absorbent inserts 50 as described in more detail above. In some embodiments, the supply 190 can be the absorbent insert web 88 described above with a series of connected absorbent inserts 50 as illustrated in FIG. 6. The method can further include attaching the absorbent inserts 50 of the present invention to the leg elastic covering web 150 and/or the first body panel web 110 and/or the second body panel web 120 in a spaced apart manner (such as at cut-and-rotate attachment station 191). In such an embodiment, the series of absorbent inserts 50, the leg elastic covering web 150, the front and back body panel webs 110, 120, the leg elastic members 140, 142, and the optional waistband webs 170, 180 together define the composite garment web 160. The method can further include folding the composite garment web 160 along a centerline 104 that extends in the machine direction 102 (such as at folding station 164), such that the first body panel web waist edge 111 is brought into close proximity with the second body panel web waist edge 121, and/or such that the first waistband web distal edge 174 is brought into close proximity with the second waistband web distal edge 184. The method in particular embodiments further includes attaching the first body panel web 110 to the second body panel web 120 along a series of garment side seam bonds 284 spaced apart in the machine direction 102. The method further includes cutting the composite garment web 160 at a series of cut locations spaced apart in the machine direction 102 to create the plurality of pant-like disposable absorbent garments 220. The seaming and cutting operations can occur at separate stations, or can occur at a single seaming and cutting station 166, as representatively illustrated in FIG. 6.

Figure 7:
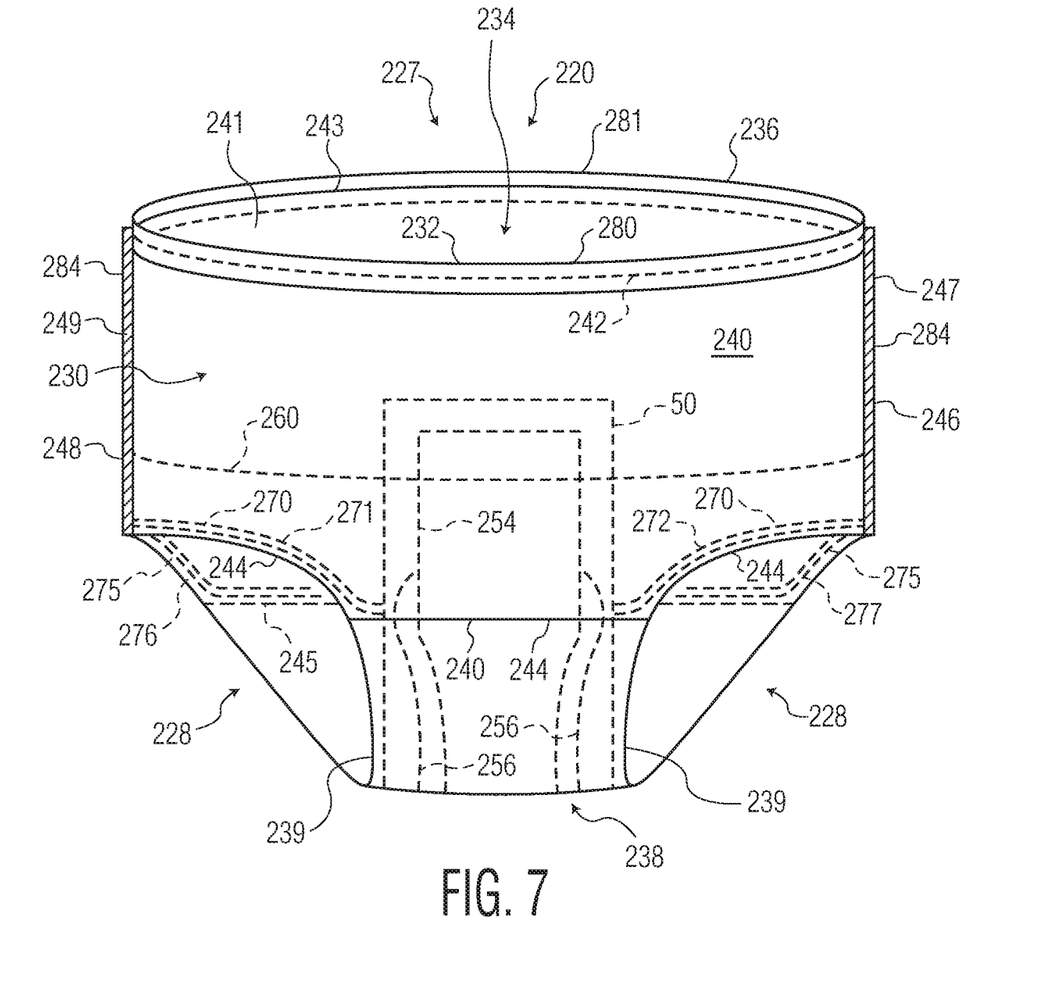
FIG. 7 is a front view of an exemplary absorbent article resulting from the methods of the present invention.

An exemplary garment 220 resulting from the absorbent core assembly method 10 and the garment assembly method 100 of the present invention is illustrated in FIG. 7. The garment 220 has a front region 230 defining a front waist end edge 232, a back region 234 defining a back waist end edge 236, and a crotch region 238 positioned longitudinally between the front region 230 and the back region 234. The crotch region 238 defines two laterally opposed crotch side edges 239. The garment 220 defines a garment length that extends from the front waist end edge 232 to the back waist end edge 236.

The garment 220 can include an elastomeric film laminate front panel 240 which defines a front panel waist edge 242, a front panel leg edge 244 spaced longitudinally inward from the front panel waist edge 242, and first and second laterally opposed front panel side edges 246, 248 which extend longitudinally between the front panel waist edge 242 and the front panel leg edge 244. The garment 220 can also include an elastomeric film laminate back panel 241 which defines a back panel waist edge 243, a back panel leg edge 245 spaced longitudinally inward from the back panel waist edge 243, and first and second laterally opposed back panel side edges 247, 249 which extend longitudinally between the back panel waist edge 243 and the back panel leg edge 245.

The garment 220 can further include at least one front leg elastic member 270 disposed adjacent the front panel leg edge 244, and at least one back leg elastic member 275 disposed adjacent the back panel leg edge 245. Examples of suitable leg elastic materials include elastics similar to the elastic members discussed above in conjunction with the garment assembly method 100 aspect of the invention. In particular embodiments, the back leg elastic member 275 and/or the front leg elastic member 270 extends laterally across the entire garment width. In other embodiments, such as that representatively illustrated in FIG. 7, the back leg elastic member 275 can comprise a pair of back leg elastic members, such as first and second back leg elastic members 276, 277 positioned on opposite sides of the absorbent insert 50. Similarly, the front leg elastic member 270 can comprise a pair of front leg elastic members, such as first and second front leg elastic members 271, 272 positioned on opposite sides of the absorbent composite 50. In some embodiments, such as that representatively illustrated in FIG. 7, each back leg elastic member 275 can comprise a plurality of elastomeric threads, and/or each front leg elastic member 270 can comprise a plurality of elastomeric threads.

The garment 220 can also include a leg elastic covering panel 260 which extends between and interconnects the front panel 240 to the back panel 241. Optionally the covering panel 260 can be comprised of a non-elastomeric nonwoven material, such as a spunbond, a spunbond laminate, a bonded-carded web, or the like, examples of which are known in the art. The front leg elastic member 270 is sandwiched between the leg elastic covering panel 260 and the front panel 240, and the back leg elastic member 275 is sandwiched between the leg elastic covering panel 260 and the back panel 241.

In particular embodiments, the front region 230 can further include a front elastomeric waistband 280 attached to the front panel 240 adjacent the front panel waist edge 242, and/or the back region 234 can include a back elastomeric waistband 281 attached to the back panel 241 adjacent the back panel waist edge 243. A pair of side seams 284, 284 connects the front region 230 to the back region 234, such that the garment 220 defines a waist opening 227 and a pair of leg openings 228. The side seams can be permanent but tearable, such as by way of adhesive, thermal, or ultrasonic bonding, or can be more readily releasable as well as refastenable, such as via the use of mechanical fastening elements.

While the invention has been described in detail with respect to specific embodiments thereof, it will be appreciated that those skilled in the art, upon attaining understanding of the foregoing will readily appreciate alterations to, variations of, and equivalents to these embodiments. Accordingly, the scope of the present invention should be assessed as that of the appended claims and any equivalents thereto. Additionally, all combinations and/or sub-combinations of the disclosed embodiments, ranges, examples, and alternatives are also contemplated.

The invention claimed is:

1. A method of applying elastic members comprising,
providing a back sheet web having a first lateral side edge and a second lateral side edge, the back sheet web defining a back sheet width extending from the first lateral side edge to the second lateral side edge,
providing a top sheet web having a first lateral side edge and a second lateral side edge, the top sheet web defining a top sheet width extending from the first lateral side edge to the second lateral side edge,
providing a plurality of discrete absorbent cores,
providing a first elastic member web and a second elastic member web,
applying a first adhesive in a first adhesive pattern to define a first adhesive application width, wherein the first adhesive application width is at least 90% the top sheet width or the back sheet width,
intermittently applying a second adhesive in a second adhesive pattern to define alternating hold zones and release zones, wherein the second adhesive has a different composition and properties than the first adhesive,
positioning the first elastic member web, the second elastic member web, the first adhesive, the second adhesive, and the discrete absorbent cores between the top sheet web and the back sheet web to define an absorbent insert web, wherein the first elastic member web and the second elastic member web are positioned in an elongated condition and a first portion of the first elastic member web and a first portion of the second elastic member web are positioned in contact with the first adhesive and the second adhesive in the hold zones and wherein a second portion of the first elastic member web and a second portion of the second elastic member web are positioned in contact with the first adhesive but not the second adhesive in the release zones, severing the first elastic member web and the second elastic member web in the release zones to define first and second discrete elastic members, retracting the second portions of the first elastic member and the second elastic member through the first adhesive in the release zones and maintaining the elongation of the first portions of the first elastic member and the second elastic member in the hold zones.

2. The method of claim 1 further comprising applying the first elongated elastic member web and the second elongated elastic member web in elastic patterns having curved portions separated by straight portions.

3. The method of claim 2 wherein the absorbent cores define a width having a narrowed portion and wherein the curved portions of the elastic patterns align with the narrowed portion of the absorbent cores.

4. The method of claim 2 further comprising aligning the curved portions of the elastic patterns with the hold zones and aligning the straight portions of the elastic patterns with the release zones.

5. The method of claim 4 wherein the elastic member web defines a width in the cross-machine direction and the second adhesive application defines a second adhesive application width defined in the cross machine direction and wherein the adhesive application width is at least twice the elastic member web width.

6. The method of claim 1 wherein the first adhesive is a construction adhesive comprising poly alpha olefin and the second adhesive is an elastic adhesive comprising a styrenic block copolymer.

7. The method of claim 6 wherein the second adhesive overlays the first adhesive in the hold zones once assembled in the absorbent insert web.

8. The method of claim 6 further comprising applying the first adhesive in a slot coat application at an add-on of 1 to 3 gsm and applying the second adhesive in a swirl pattern at an add-on of 8 to 12 gsm.

9. The method of claim 8 wherein applying the first adhesive further comprises applying a slot coat pattern having a plurality of voids extending in a machine direction, each void having a width of 0.75 to 1.25 mm.

10. The method of claim 1 wherein the first elongated elastic member web and the second elongated elastic member web are each applied in an elastic pattern having a portion that is at least partially overlaid by the discrete absorbent cores once assembled in the absorbent insert web.

11. The method of claim 10 further comprising severing and retracting the first elongated elastic member web and the second elongated elastic member web such that the portion that is at least partially overlaid by the absorbent core is untensioned.

12. The method of claim 1 further comprising, supplying a first body panel web and a second body panel web, separating the absorbent insert web at lines of weakness located between the discrete absorbent cores to define discrete absorbent inserts, attaching the discrete absorbent inserts to the first body panel web and the second body panel web to define a composite garment web, folding the composite garment web, attaching the first body panel web to the second body panel web along a series of garment side seam bonds, and cutting the composite garment web at the garment side seam bonds to create a plurality of pant-like disposable absorbent garments.

* * * * *